(12) United States Patent
Litvak et al.

(10) Patent No.: US 8,024,046 B2
(45) Date of Patent: Sep. 20, 2011

(54) SYSTEMS FOR FITTING A COCHLEAR IMPLANT TO A PATIENT

(75) Inventors: Leonid M. Litvak, Los Angeles, CA (US); Lakshmi N. Mishra, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 18 days.

(21) Appl. No.: 12/782,085

(22) Filed: May 18, 2010

(65) Prior Publication Data

US 2010/0228321 A1    Sep. 9, 2010

Related U.S. Application Data

(63) Continuation of application No. 11/841,501, filed on Aug. 20, 2007, now Pat. No. 7,747,329, which is a continuation of application No. 10/989,521, filed on Nov. 16, 2004, now Pat. No. 7,292,892.

(60) Provisional application No. 60/523,928, filed on Nov. 21, 2003.

(51) Int. Cl.
*A61N 1/36* (2006.01)
*H04R 25/00* (2006.01)

(52) U.S. Cl. ............ 607/57; 607/55; 607/56; 607/137; 600/379; 600/559

(58) Field of Classification Search .......... 607/55, 607/56, 57, 137; 600/379, 559
See application file for complete search history.

(56) References Cited

U.S. PATENT DOCUMENTS

| | | | |
|---|---|---|---|
| 4,052,572 A * | 10/1977 | Schafer | 607/56 |
| 4,532,930 A | 8/1985 | Crosby et al. | |
| 4,819,647 A | 4/1989 | Byers et al. | |
| 5,626,629 A | 5/1997 | Faltys et al. | |
| 6,068,652 A | 5/2000 | Cohen et al. | |
| 6,129,753 A | 10/2000 | Kuzma | |
| 6,181,969 B1 | 1/2001 | Gord | |
| 6,219,580 B1 | 4/2001 | Faltys et al. | |
| 6,289,247 B1 | 9/2001 | Faltys et al. | |
| 6,393,325 B1 | 5/2002 | Mann et al. | |
| 6,810,289 B1 * | 10/2004 | Shaquer | 607/57 |
| 7,223,245 B2 | 5/2007 | Zoth et al. | |

FOREIGN PATENT DOCUMENTS

| | | |
|---|---|---|
| EP | 1338301 | 8/2003 |
| WO | 97/48447 | 12/1997 |
| WO | 02/09808 | 2/2002 |

OTHER PUBLICATIONS

Greenwood, DD, "A cochlear frequency-position function for several species—29 years later", Journal of the Acoustical Society of America, vol. 87, p. 2592-2605 (1990).

* cited by examiner

*Primary Examiner* — Carl H Layno
*Assistant Examiner* — Natasha Patel
(74) *Attorney, Agent, or Firm* — Wong, Cabello, Lutsch, Rutherford & Brucculeri LLP

(57) ABSTRACT

Systems for fitting an implantable cochlear stimulator to a patient include an interface unit configured to display a graphical representation of an implant fitting line as part of a graphical user interface. The implant fitting line has a slope and a horizontal position and represents a mapping relationship between a plurality of audio frequencies and a plurality of stimulation sites within a cochlea of the patient. The interface unit is further configured to facilitate adjustment of the slope and/or horizontal position of the fitting line.

15 Claims, 9 Drawing Sheets

SYSTEMS FOR FITTING A COCHLEAR IMPLANT TO A PATIENT

RELATED APPLICATIONS

The present application is a continuation application of U.S. application Ser. No. 11/841,501, filed Aug. 20, 2007 now U.S. Pat. No. 7,747,329, which in turn is a continuation application of U.S. application Ser. No. 10/989,521, filed Nov. 16, 2004 (now U.S. Pat. No. 7,292,892), which application claims the benefit under 35 U.S.C. §119(e) of Provisional Application Ser. No. 60/523,928, filed Nov. 21, 2003. All of these applications are incorporated herein by reference in their entireties.

BACKGROUND

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the auditory ossicles. Conductive hearing loss may often be helped by use of conventional hearing aids, which amplify sound so that acoustic information reaches the cochlea and the hair cells. Some types of conductive hearing loss are also amenable to alleviation by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural deafness, numerous cochlear implant systems—or cochlear prosthesis—have been developed which seek to bypass the hair cells in the cochlea by presenting electrical stimulation to the auditory nerve fibers directly, leading to the perception of sound in the brain and at least partial restoration of hearing function. To facilitate direct stimulation of the auditory nerve fibers, an array of electrodes which are responsive to a suitable external source of electrical stimuli and which transmit those stimuli to the auditory nerve fibers may be implanted in the cochlea.

SUMMARY

An exemplary method of fitting a cochlear implant system to a patient includes establishing an implant fitting line having a slope and a position. The implant fitting line represents a relationship between a number of stimulation sites within a cochlea of the patient and a number of corresponding audio frequencies. That is, the implant fitting line defines which locations along the length of the cochlea, when stimulated, are perceived by the patient as specific tones or frequencies. The method further includes presenting a first audio signal having a number of audio frequencies to the patient and applying a stimulus current to one or more stimulation sites corresponding to the number of audio frequencies of the first audio signal. The method further includes adjusting the slope of the fitting line based on a response of the patient to the stimulus current.

An exemplary system for fitting a cochlear implant to a patient includes an implantable cochlear stimulator with a number of stimulus channels configured to apply stimulus current to a number of stimulation sites within a cochlea of the patient. The system further includes a speech processor having a number of analysis channels configured to divide an input audio signal into a number of signals having distinct frequencies and mapping circuitry configured to map the number of signals generated by the analysis channels to the stimulus channels according to a mapping scheme. The mapping scheme is adjusted based on a change in a slope of a fitting line, the fitting line representing a relationship between the number of stimulation sites and a number of corresponding audio frequencies.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems are described herein for fitting a cochlear implant to a patient by adjusting the slope and/or position of an implant fitting line. The fitting line represents a relationship between a number of stimulation sites within a cochlea of a patient and a number of corresponding audio frequencies. A first audio signal having a number of audio frequencies is presented to the patient and a stimulus current is applied to one or more stimulation sites corresponding to the number of audio frequencies of the first audio signal. The slope of the fitting line may then be adjusted based on a response of the patient to the stimulus current corresponding to the first audio signal. A second audio signal having a number of audio frequencies is then presented to the patient and a stimulus current is applied to one or more stimulation sites corresponding to the number of audio frequencies of the second audio signal. The position of the fitting line may then be adjusted based on a response of the patient to the stimulus current corresponding to the second audio signal.

In the following description, for purposes of explanation, numerous specific details are set forth in order to provide a thorough understanding of the present system and method. It will be apparent, however, to one skilled in the art that the present system and method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
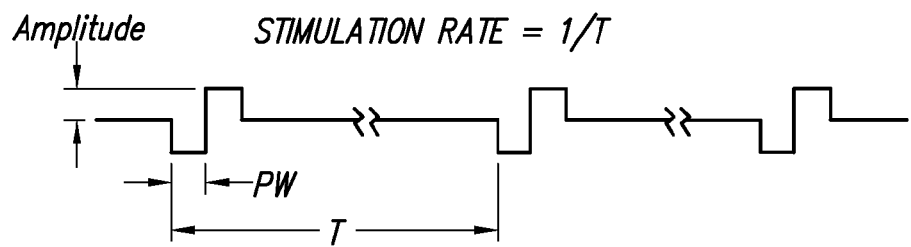
FIG. 1 shows a waveform diagram of a biphasic pulse train that may be used by a cochlear implant system in order to produce a desired therapeutic effect according to principles described herein.

FIG. 1 shows a waveform diagram of a biphasic pulse train (11) that may be used by a cochlear implant system in order to produce a desired therapeutic effect. The waveform shown defines stimulation rate (1/T), pulse width (PW) and pulse amplitude. A biphasic pulse train (11) may be used in connection with any neurostimulator device, such as a cochlear implant system, a spinal cord stimulator (SCS), a deep brain stimulator (DBS) or other neural stimulator.

As shown in FIG. 1, a "biphasic" pulse (11) may include two pulses: a first pulse of one polarity having a specified magnitude, followed immediately, or after a short delay, by a second pulse of the opposite polarity having the same total charge, which charge is the product of stimulus current multiplied by the duration of each pulse or phase. Such "charge balancing" may prevent tissue damage at the site of stimulation and prevent electrode corrosion.

Figure 2:
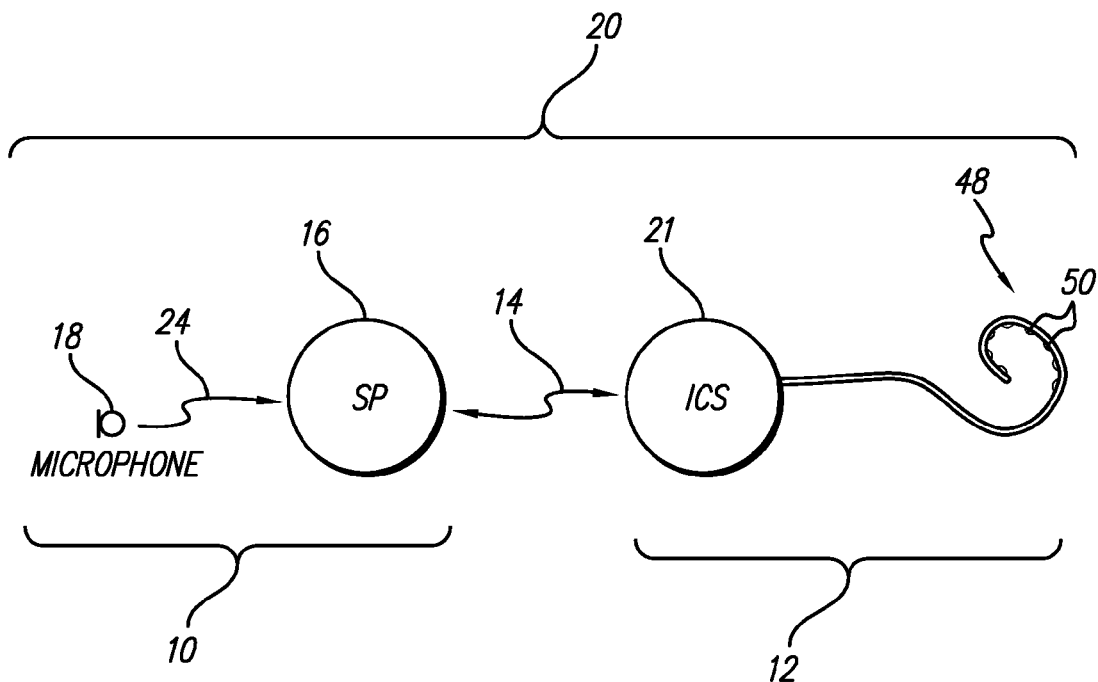
FIG. 2 shows an exemplary cochlear implant system according to principles described herein.

FIG. 2 shows an exemplary cochlear implant system (20). The cochlear implant system (20) includes a speech processor portion (10) and a cochlear stimulation portion (12). The speech processor portion (10) may include a speech processor (SP) (16), a microphone (18), and/or additional circuitry as best serves a particular application. The cochlear stimulation portion (12) may include an implantable cochlear stimulator (ICS) (21), an electrode array (48), and/or additional circuitry as best serves a particular application. The components within the speech processor portion (10) and the cochlear stimulation portion (12) will be described in more detail below.

The microphone (18) of FIG. 2 is configured to sense acoustic signals and convert such sensed signals to corresponding electrical signals. The electrical signals are sent to the SP (16) over an electrical or other link (24). Alternatively, the microphone (18) may be connected directly to the SP (16). The SP (16) processes these converted acoustic signals in accordance with a selected speech processing strategy to generate appropriate control signals for controlling the ICS (21). These control signals may specify or define the polarity, magnitude, location (i.e., which electrode pair or electrode group receive the stimulation current), and timing (i.e., when the stimulation current is to be applied to a particular electrode pair) of the stimulation current that is generated by the ICS (21).

The electrode array (48) of FIG. 2 is adapted to be inserted within a duct of the cochlea. As shown in FIG. 2, the array (48) includes a multiplicity of electrodes (50), e.g., sixteen electrodes, spaced along its length. Each of the electrodes (50) is selectively connected to the ICS (21). The electrode array (48) may be substantially as shown and described in U.S. Pat. Nos. 4,819,647 or 6,129,753, each of which is incorporated herein by reference in its entirety. Electronic circuitry within the ICS (21) is configured to apply stimulation current to selected pairs or groups of the individual electrodes (50) included within the electrode array (48) in accordance with a specified stimulation pattern defined by the SP (16).

The ICS (21) and the SP (16) may be electronically connected via a suitable data or communications link (14). In some embodiments, the SP (16) and the microphone (18) comprise an external portion of the cochlear implant system (20) and the ICS (21) and the electrode array (48) comprise an implantable portion of the system (20). In alternative embodiments, one or more portions of the SP (16) are included within the implantable portion of the cochlear implant system (20). The implantable portion of the cochlear implant system (20) is implanted within the patient's body. Thus, the data link (14) is a transcutaneous (through the skin) data link that allows power and control signals to be sent from the SP (16) to the ICS (21). In some embodiments, data and status signals may also be sent from the ICS (21) to the SP (16).

The external and implantable portions of the cochlear implant system (20) may each include one or more coils configured to transmit and receive power and/or control signals via the data link (14). For example, the external portion of the cochlear implant system (20) may include an external coil (not shown) and the implantable portion of the cochlear implant system (20) may include an implantable coil (not shown). The external coil and the implantable coil may be inductively coupled to each other, thereby allowing data to be transmitted between the external portion and the implantable portion. The data may include, for example, the magnitude and polarity of a sensed acoustic signal. The external coil may also transmit power from the external portion to the implantable portion of the cochlear implant system (20). It will be noted that, in some embodiments, both the SP (16) and the ICS (21) may be implanted within the patient, either in the same housing or in separate housings. If the SP (16) and the ICS (21) are in the same housing, the link (14) may be realized with a direct wire connection within such housing. If the SP (16) and the ICS (21) are in separate housings, the link (14) may be an inductive link, for example.

Figure 3:
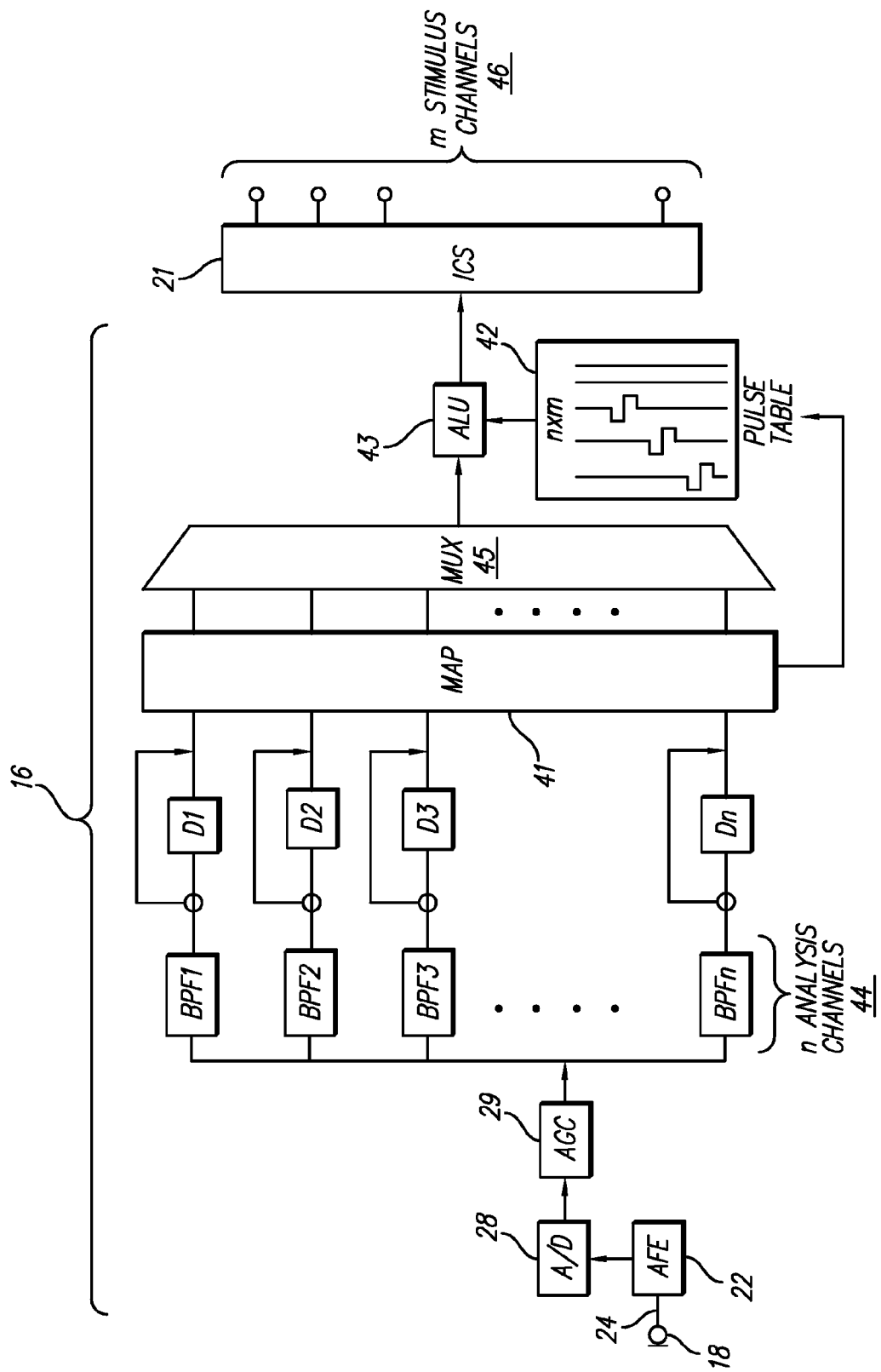
FIG. 3 is a functional block diagram of an exemplary speech processor and an exemplary implantable cochlear stimulator according to principles described herein.

FIG. 3 is a functional block diagram of an exemplary SP (16) and ICS (21). The functions shown in FIG. 3 are merely representative of the many different functions that may be performed by the SP (16) and/or the ICS (21). A complete description of the functional block diagram of the SP (16) and the ICS (21) is found in U.S. Pat. No. 6,219,580, which is incorporated herein by reference in its entirety.

As shown in FIG. 3, the microphone (18) senses acoustic information, such as speech and music, and converts the acoustic information into one or more electrical signals. These signals are then amplified in audio front-end (AFE) circuitry (22). The amplified audio signal is then converted to a digital signal by an analog-to-digital (A/D) converter (28). The resulting digital signal is then subjected to automatic gain control using a suitable automatic gain control (AGC) function (29).

After appropriate automatic gain control, the digital signal is then processed in one of a number of digital signal processing or analysis channels (44). For example, the SP (16) may include, but is not limited to, eight analysis channels (44). Each analysis channel (44) may respond to a different frequency content of the sensed acoustical signal. In other words, each analysis channel (44) includes a band-pass filter (BP1-BPFn) or other type of filter such that the digital signal is divided into n frequency channels. The lowest frequency filter may be a low-pass filter, and the highest frequency filter may be a high-pass filter.

As shown in FIG. 3, each analysis channel (44) may also include a detection stage (D1-Dn). Each detection stage (D1-Dn) may include an energy detection circuit (not shown), which may be realized, e.g., through a rectification circuit followed by an integrator circuit. As shown in FIG. 3, each of the detection stages (D1-Dn) may alternatively be bypassed depending on the particular signal processing strategy being used.

After energy detection, or bypassing of such, the signal from each of the n analysis channels (44) is forwarded to a mapping stage (41). The mapping stage (41) may be configured to map the signals in each of the analysis channels (44) to one or more of the m stimulus channels (46). The mapping stage (41) may be further configured to perform additional processing of the signal, such as signal compression. The signals output by each analysis channel (44) may then be serialized by a multiplexer (45) into one serial data channel. The multiplexed signal may then be further processed according to information included in a pulse table (42) connected to an arithmetic logic unit (ALU) (43). After the signal is appropriately processed, compressed, and mapped, the signal may be input into the ICS (21) to control the actual stimulus patterns that are applied to the patient via the electrode array (48; FIG. 2).

As mentioned, each of the n analysis channels (44) may be mapped to one or more stimulus channels (46). In other words, the information contained in the n analysis channels (44) controls the stimulus patterns that are applied to the patient by the ICS (21) and its associated electrode array (48; FIG. 2). Stimulus current may be applied to any number of stimulation sites within the patient's cochlea via the m stimulus channels (46). As used herein and in the appended claims, the term "stimulation site" will be used to refer to a target area or location to which the stimulus current is applied. For example, a stimulation site may refer to a particular location in the tissue of a cochlear implant patient. As will be described in more detail below, through appropriate weighting and sharing of currents between the electrodes (50; FIG. 2), stimulus current may be applied to any stimulation site along the length of the electrode array (48; FIG. 2).

Figure 4:
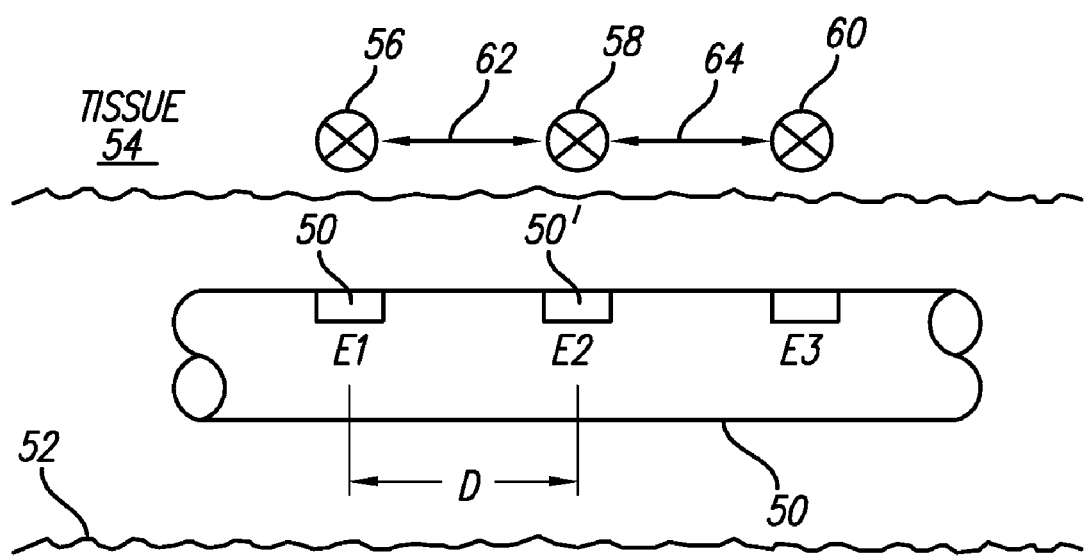
FIG. 4 is a diagram illustrating various possible stimulation sites in the tissue of a patient according to principles described herein.

FIG. 4 is a diagram illustrating various possible stimulation sites in the tissue of a patient. As shown in FIG. 4, an electrode array (48) having three electrodes E1-E3 may be inserted into a duct (52) within tissue (54) that is to be stimulated by stimulus current. The electrode array (48) has three electrodes for illustrative purposes only. It will be recognized that the electrode array (48) may have any number of electrodes. The duct (52) may be, but is not limited to, the scala tympani of the cochlea of a cochlear implant patient. The electrodes E1-E3 may be spaced apart from each other by a distance "D".

A reference electrode (not shown) may also be present some distance from the electrodes E1-E3, thereby allowing monopolar stimulation to occur between a selected one of the electrodes and the reference electrode. Bipolar stimulation may also occur, e.g., between electrodes E1 and E2, between E2 and E3, or between any other pair of electrodes. Other types of stimulation patterns may also or alternatively be used as best serves a particular application. For example, a first electrical pulse may presented on electrode E2 at the same time as a second electrical pulse of opposite polarity but of smaller amplitude is presented on electrodes E1 and E3.

The analysis channels (44; FIG. 3) may be mapped to the stimulus channels (46; FIG. 3) according to a number of different mapping schemes. For example, the analysis channels (44; FIG. 3) may be mapped to the stimulus channels (46; FIG. 3) such that each electrode E1-E3 corresponds to one of the analysis channels (44; FIG. 3). In this case, stimulus current applied via electrode E1 stimulates a first stimulation site (56) in the tissue (54). Likewise, stimulus current applied via electrode E2 stimulates a second stimulation site (58) in the tissue (54) and stimulus current applied via electrode E3 stimulates a third stimulation site (60) in the tissue (54). As shown in FIG. 4, the stimulation sites (56, 58, 60) are located adjacent to the physical location of their respective electrodes E1-E3.

However, in some embodiments, different mapping schemes other than a one-to-one mapping scheme may be used. For example, a single analysis channel (44; FIG. 3) may be mapped to multiple stimulus channels (46; FIG. 3). Such mapping may result in stimulus current being shared between two electrodes such as E1 and E2 or any other pair of electrodes. By sharing the stimulus current between electrodes E1 and E2, for example, the effective tissue location where the stimulus current is applied may be anywhere along the line (62). Likewise, if the stimulus current is shared between electrodes E2 and E3, the stimulus site may be anywhere along the line (64). In general, the stimulus site may be anywhere along the lines (62, 64).

To illustrate further, suppose a stimulus current having an amplitude I1 is applied to the tissue through electrode E1 (and some reference electrode). The stimulation site within the tissue (54) where the stimulus current would be felt by the patient would be the first stimulation site (56). However, if a stimulus current of only 0.9 multiplied by I1 were applied through electrode E1 at the same time that a stimulus current of 0.1 multiplied by I1 where applied through electrode E2, then the location within the tissue (54) where the stimulus current would be felt would be a little to the right of the first stimulation site (56) along the line (62).

Hence, as shown in the preceding examples, the stimulation site may be at any location along the tissue corresponding to the physical location of the electrode array (48; FIG. 2), even though there are only a fixed number of electrodes (50; FIG. 2). A concept of "virtual electrodes" is useful in illustrating the fact that there may be an unlimited number of stimulation sites even though there are only a fixed number of electrodes (50; FIG. 2). For example, any number of virtual electrodes may exist in between any two physical electrodes (50; FIG. 2). Each virtual electrode may have a corresponding stimulation site along the tissue adjacent to the line in between the two physical electrodes (50; FIG. 2). One method of achieving virtual electrodes is known as current steering. Current steering provides concurrent, weighted currents at two electrodes (50; FIG. 2), as described in the examples above. Another method for achieving virtual electrodes is known as time-multiplexed, non-simultaneous presentation of stimuli and comprises rapidly and alternately providing stimulus current to two closely placed electrodes.

Figure 5:
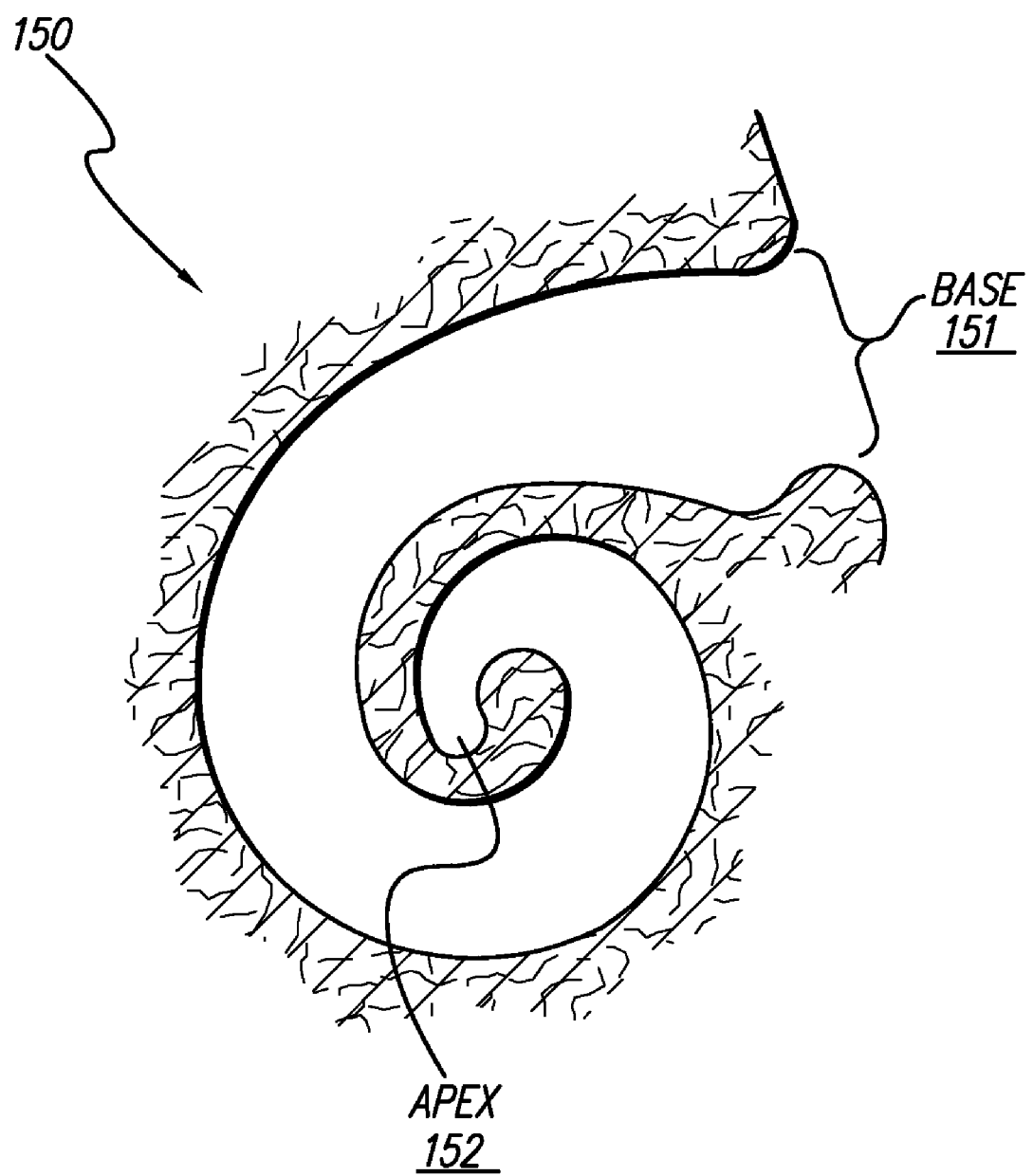
FIG. 5 is a diagram of an exemplary cochlea according to principles described herein.

FIG. 5 is a diagram of an exemplary cochlea (150). As shown in FIG. 5, the cochlea (150) is in the shape of a spiral beginning at a base (151) and ending at an apex (152). The nerve cells within the cochlea (150) are arranged in an orderly tonotopic sequence, from high frequencies at the basal end (151) to progressively lower frequencies toward the apex (152). Hence, each location along the length of the cochlea (150) corresponds to a different perceived audio frequency. In other words, the application of a stimulus current at a particular location within the cochlea (150) of a cochlear implant patient results in the patient perceiving a distinct audio frequency corresponding to that location.

Figure 6:
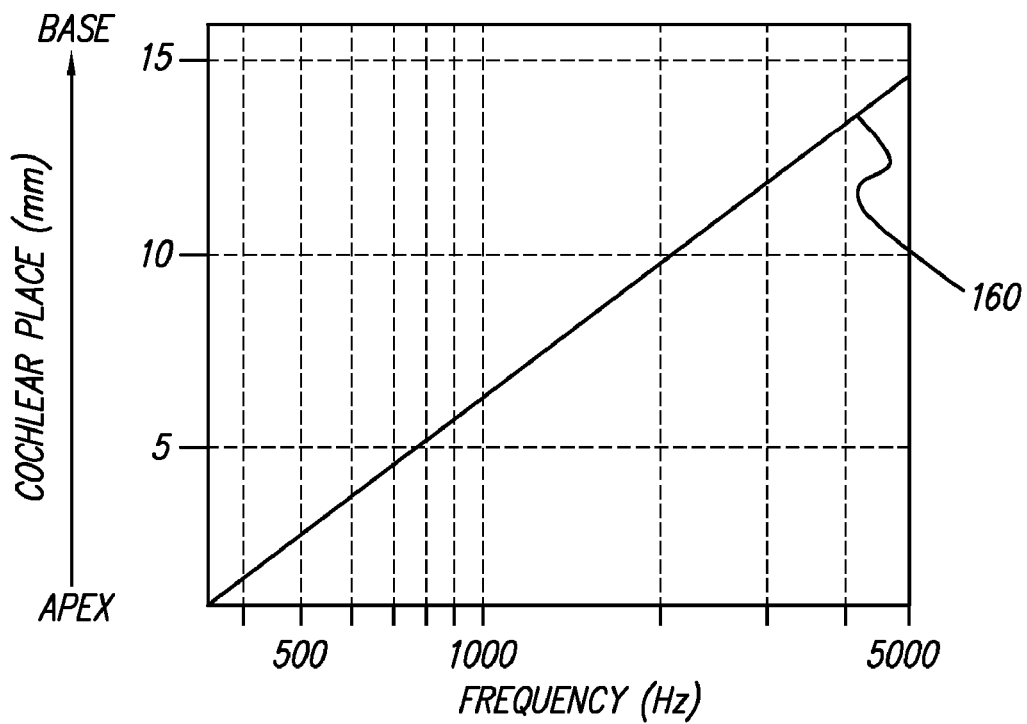
FIG. 6 shows the relationship between location within the cochlea and perceived audio frequency according to principles described herein.

FIG. 6 shows the relationship between location within the cochlea (150; FIG. 5) and perceived audio frequency (Hz). The horizontal axis of the graph in FIG. 6 represents frequency (Hz) in a logarithmic scale and the vertical axis of the graph represents the location (mm) along the cochlea (150; FIG. 5) beginning at the apex (152; FIG. 5) and extending towards the base (151; FIG. 5). FIG. 6 shows an exemplary line (160) which will be referred to herein as an "intrinsic line" having an "intrinsic slope" for an individual cochlea (150; FIG. 5). The "intrinsic slope," or just slope, refers to the change in position within the cochlea (150; FIG. 5) divided by the change in perceived frequency between two points on the intrinsic line (160).

The exemplary intrinsic line (160) represents the relationship between location within the cochlea (150; FIG. 5) and actual perceived audio frequency across a specified band of frequencies. It has been discovered empirically that the intrinsic line (160) is approximately linear for a large part of the perceived hearing range of frequencies when the frequencies are represented by a logarithmic scale, as shown in FIG. 6. Hence, as illustrated by the intrinsic line (160), a patient perceives lower frequencies at locations near the apex (152; FIG. 5) and progressively higher frequencies at locations closer to the base (151; FIG. 5).

Figure 7:
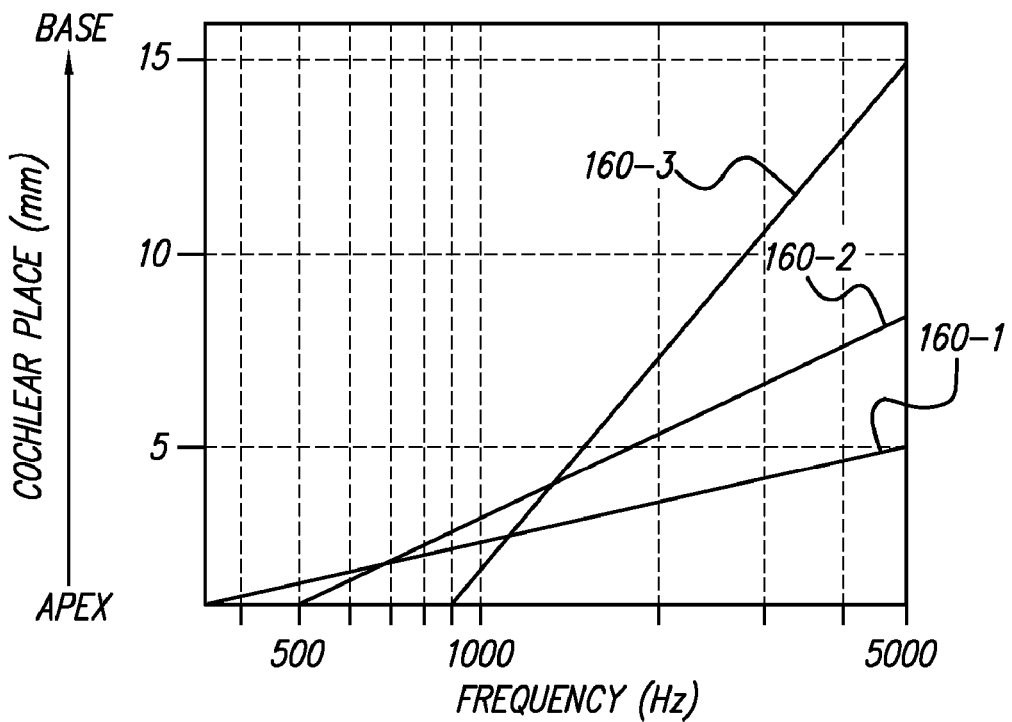
FIG. 7 shows a number of exemplary intrinsic lines each having a different slope and position according to principles described herein.

The relationship between position within the cochlea (150; FIG. 5) and perceived audio frequency is different for every individual because no two cochleas (150; FIG. 5) are anatomically alike and because the nerve wiring between the cochlea (150; FIG. 5) and the brain is different for every individual. Hence, each cochlea (150; FIG. 5) has a distinct intrinsic line (160) that may differ from intrinsic lines corresponding to other cochleas (150; FIG. 5) in shape, slope, and/or position. For example, FIG. 7 shows a number of exemplary intrinsic lines (160-1, 160-2, 160-3) each having a different slope and position representing the characteristics of different cochlea. It will be recognized that the intrinsic lines (160-1, 160-2, 160-3) are merely exemplary and may have any slope and position as determined by the physiological characteristics of the corresponding cochleas (150; FIG. 5).

Figure 8:
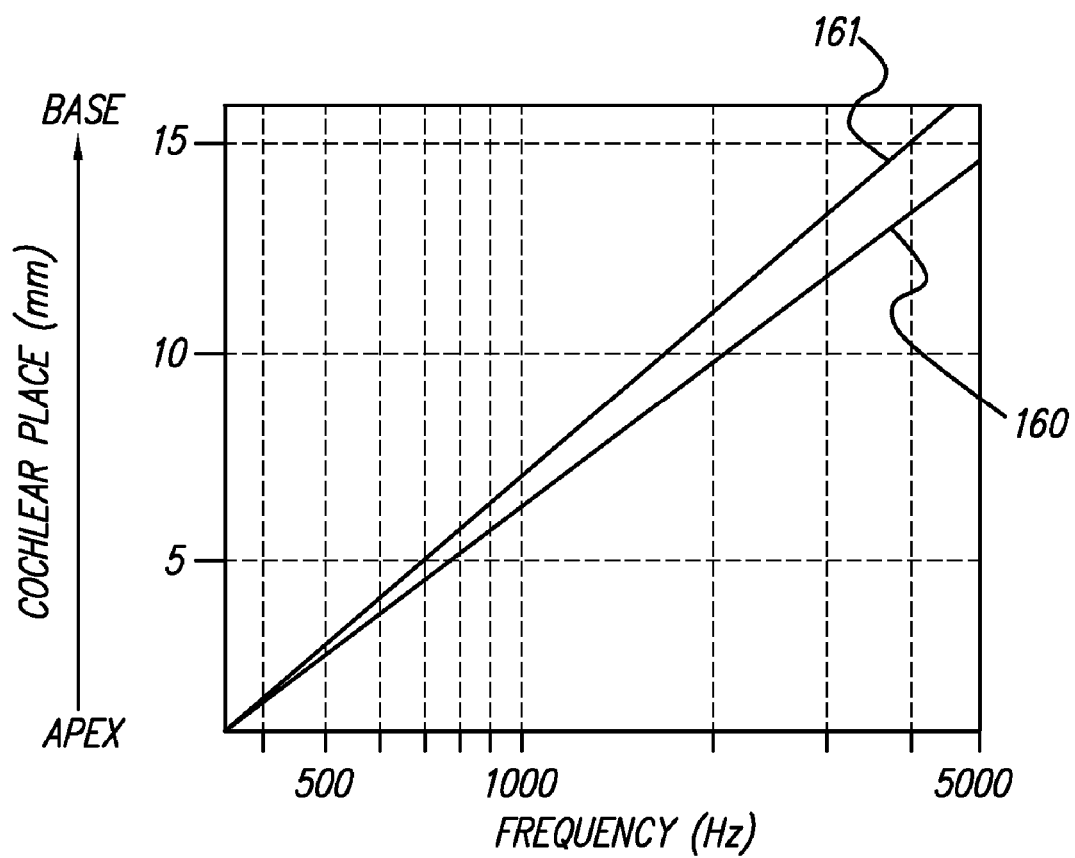
FIG. 8 shows an exemplary implant fitting line plotted on the same graph as the intrinsic line according to principles described herein.

Because the intrinsic line (160) is different for each cochlear implant patient, the cochlear implant system (20; FIG. 2) may be "fitted" to each patient. For example, the analysis channels (44; FIG. 3) of the SP (16; FIG. 3) may be mapped to one or more stimulus channels (46; FIG. 3) within the ICS (21; FIG. 3) using an initial mapping scheme. This initial mapping scheme results in an "implant fitting line." The implant fitting line represents the relationship between location within the cochlea (150; FIG. 5) and predicted perceived audio frequency across a specified band of frequencies. That is, the implant fitting line defines which locations along the length of the cochlea, when stimulated, are perceived by the patient as specific tones or frequencies. For example, FIG. 8 shows an exemplary implant fitting line (161) plotted on the same graph as the intrinsic line (160). The fitting line (161) and the intrinsic line (160) correspond to a particular cochlear implant patient.

The particular mapping scheme used to generate the fitting line (161) predicts that stimulus current applied to any place along the cochlea (150; FIG. 5) will result in the patient perceiving a corresponding frequency, as defined by the fitting line (161). For example, if an incoming tone with a frequency equal to 1700 Hz is picked up or generated by the cochlear implant system (20; FIG. 2), a stimulus current will be applied to a location approximately equal to 10 mm from the apex of the cochlea (150; FIG. 5), as defined by the fitting line (161).

However, as shown in FIG. 8, the fitting line (161) is often misaligned with the intrinsic line (160). In other words, the implant fitting line (161) has a different slope and/or position than the intrinsic line (160). This misalignment is sometimes referred to as "pitch warping" and is due to the fact that the intrinsic line (160) is different for each cochlear implant system (20; FIG. 2). The misalignment of the implant fitting line (161) and the intrinsic line (160) causes the patient to actually perceive a frequency that is different than the frequency picked up or generated by the cochlear implant system (20; FIG. 2). Referring again to the example wherein the 1700 Hz tone is picked up by the cochlear implant system (20; FIG. 2) and stimulus current is applied to a location approximately equal to 10 mm from the apex of the cochlea (150; FIG. 5), the patient will actually perceive a tone having a frequency substantially equal to 2000 Hz as shown by the intrinsic line (160) instead of perceiving a 1700 Hz tone as predicted by the fitting line (161).

Hence, as illustrated by the example given in connection with FIG. 8, the fitting line (161) should be substantially equal to the intrinsic line (160) in order for the cochlear implant patient to properly perceive audio signals input into the cochlear implant system (20; FIG. 2). As will be described below in more detail, the slope and/or the position of the fitting line (161) may be modified such that incoming audio signals are properly perceived by the cochlear implant patient.

As mentioned, the fitting line (161) may have a different slope and/or position than the intrinsic line (160). A fitting line (161) with a different slope than the slope of the intrinsic line (160) affects the relative alignment of frequencies perceived by the cochlear implant patient. For example, a fitting line (161) with an incorrect slope may cause music or other audio signals that depend on relative frequencies to be perceived by a cochlear implant patient as being harmonically out of tune. However, if the fitting line (161) has the same slope as the intrinsic line (160), even if the position of the fitting line (161) does not match the position of the intrinsic line (160), the patient may recognize the music because the perceived frequencies are in a correct harmonic relationship.

Figure 9:
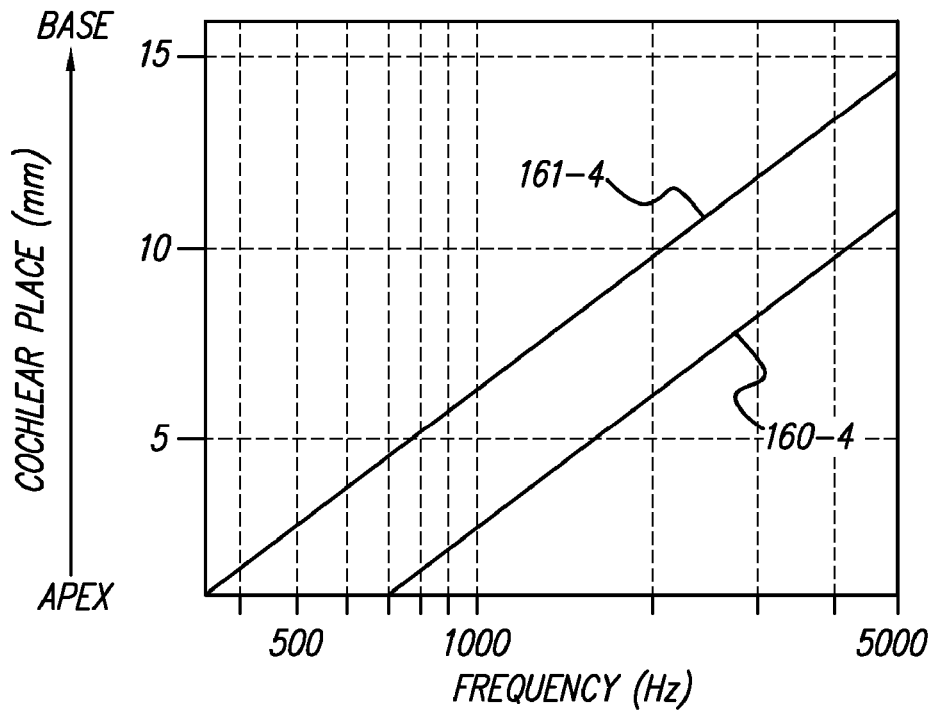
FIG. 9 shows a graph wherein the fitting line is offset to the left of the intrinsic line according to principles described herein.

A fitting line (161) with a different position than the position of the intrinsic line (160) affects the overall pitch of an audio signal perceived by the cochlear implant patient. In other words, the overall pitch of an audio signal may be perceived by the cochlear implant patient as being too low or too high. For example, FIG. 9 shows a graph in which the fitting line (161-4) is offset to the left of the intrinsic line (160-4). In other words, the horizontal axis intercept of the fitting line (161-4) is to the left of the horizontal axis intercept of the intrinsic line (161-4). The horizontal axis is also referred to as the X-axis. If the fitting line (161-4) is offset to the left of the intrinsic line (160-4), as shown in FIG. 9, the overall pitch of the audio signal is perceived by the cochlear implant patient as being too high.

Figure 10:
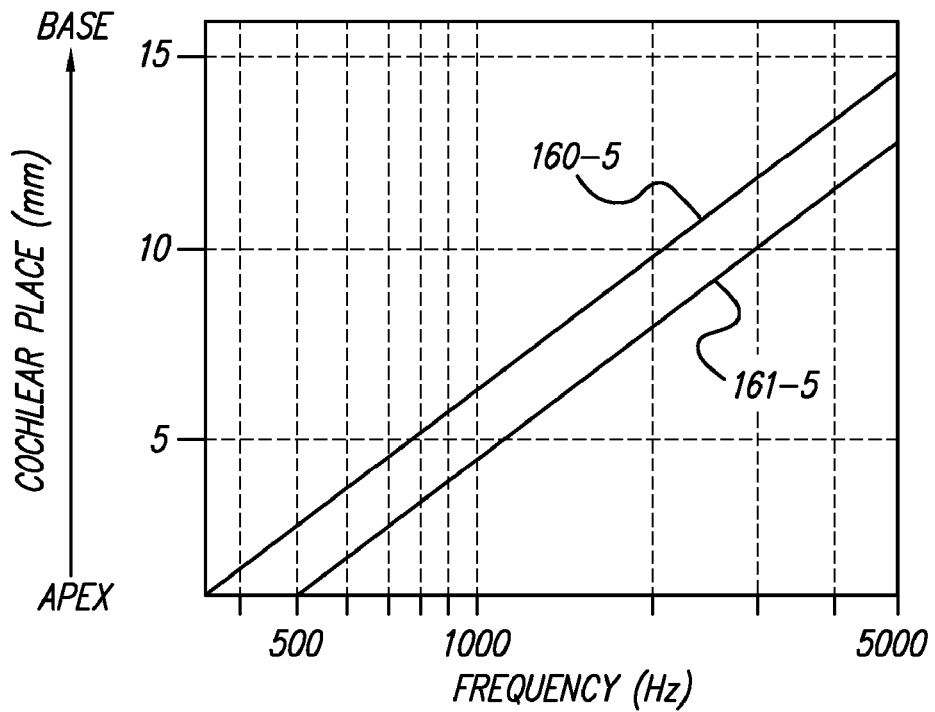
FIG. 10 shows a graph wherein the fitting line is offset to the right of the intrinsic line according to principles described herein.

On the other hand, FIG. 10 shows a graph in which the fitting line (161-5) is offset to the right of the intrinsic line (160-5). In other words, the X-axis intercept of the fitting line (161-4) is to the right of the X-axis intercept of the intrinsic line (161-4). If the fitting line (161-5) is offset to the right of the intrinsic line (160-5), as shown in FIG. 10, the overall pitch of the audio signal is perceived by the cochlear implant patient as being too low.

The effect of the fitting line (161; FIG. 8) being offset from the intrinsic line (160; FIG. 8) is particularly evident in sounds having a characteristic pitch, such as human speech. The presence of an offset, for example, can cause the cochlear implant patient to perceive human speech as being too high or "squeaky." The offset may alternatively cause the cochlear implant patient to perceive human speech as being too low or slow.

Figure 11:
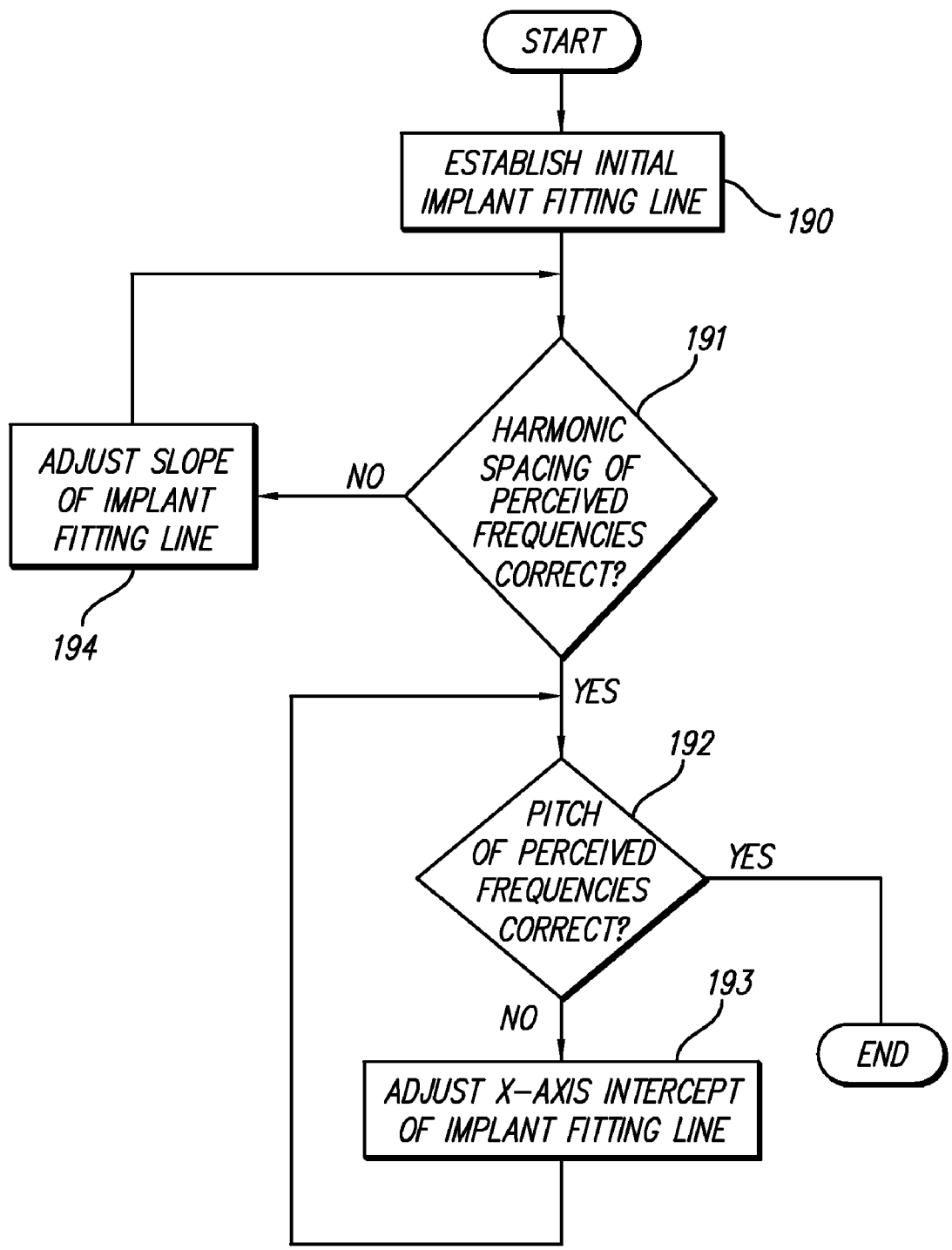
FIG. 11 is a flow chart illustrating an exemplary method of fitting a cochlear implant system to a cochlear implant patient by modifying the implant fitting line according to principles described herein.

FIG. 11 is a flow chart illustrating an exemplary method of fitting a cochlear implant system (20; FIG. 2) to a cochlear implant patient by modifying the implant fitting line (161; FIG. 8). As shown in FIG. 11, an initial fitting line (161; FIG. 8) is first established (step 190). The initial fitting line (161; FIG. 8) may be chosen based on an average of intrinsic slopes (160; FIG. 8) of a number of different individuals. Alternatively, the initial fitting line (161; FIG. 8) may be chosen based on any other criteria. The next step, as shown in FIG. 11, is determining whether the harmonic spacing of the frequencies perceived by the cochlear implant patient is correct (step 191). In some embodiments, the patient and/or a clinician may make that determination using a musical tune familiar to the patient. For example, a musical tune familiar to the patient, such as a simple melody, may be presented to the patient. Locations along the cochlea (150; FIG. 5) corresponding to the frequency of each note in the tune are then stimulated according to the relationship defined by the fitting line (161; FIG. 8).

Because the tune is familiar to the patient, the relationship of notes within the tune may be assessed by the patient as being harmonically correct or not harmonically correct. In many instances, the cochlear implant patient does not have to have musical training to identify whether the frequency range of the tune is too compressed (i.e., the notes sound too much alike) or whether the frequency range of the tune is too expansive (i.e., the notes are perceived to be too far apart). It will be recognized that many different audio signals other than musical tunes may be used to determine whether the spacing of the frequencies perceived by the cochlear implant patient is correct (step 191). In general, the determination may be made by presenting any audio signal having a recognizable range of frequencies to the patient.

If the harmonic spacing of the frequencies perceived by the cochlear implant patient is not correct (No; step 191), the slope of the implant fitting line (161; FIG. 8) is adjusted (step 194). The slope of the implant fitting line (161; FIG. 8) is adjusted until the harmonic spacing of the frequencies perceived by the patient is correct (Yes; step 191). In some embodiments, the same musical tune or other audio signal is presented to the patient each time after the implant fitting line (161; FIG. 8) is adjusted. This process may be repeated until the musical tune or other audio signal is perceived by the patient as being harmonically correct. Once the harmonic spacing of the frequencies perceived by the patient is correct (Yes; step 191), the slope of the implant fitting line (161; FIG. 8) is substantially equal to the slope of the intrinsic line (160; FIG. 8).

The patient then determines whether the pitch of the perceived frequencies is correct (step 192). In some embodiments, the patient and/or a clinician may make that determination using a sound having a pitch known to the patient. For example, human speech may be presented to the patient. Human speech is used in many situations because the human hearing system, including the associated nervous system, is especially sensitive to the pitch of human speech. However, any other sound having a known pitch may be used to determine whether the pitch of the perceived frequencies is correct (step 192).

If the pitch of a sound presented to the patient is either too high or too low (No; step 192), the position of the fitting line (161; FIG. 8) may be adjusted by adjusting the X-axis intercept of the implant fitting line (step 193) until the pitch of the perceived frequencies of the sound is correct (Yes; step 192). For example, if male speech is presented to the patient and the patient perceives the speech as being too high, the X-axis intercept of the fitting line may be adjusted to the right to lower the overall pitch of the speech. Likewise, if the male speech is perceived as being too low, the X-axis intercept of the fitting line (161; FIG. 8) may be adjusted to the left to increase the overall pitch of the speech. When the pitch of the perceived frequencies of the sound is correct (Yes; step 192), the position of the fitting line (161; FIG. 8) will be substantially equal to the position of the intrinsic line (160; FIG. 8).

The above described methods of adjusting the slope and/or position of the fitting line (161; FIG. 8) such that the fitting line (161; FIG. 8) substantially matches the intrinsic line (160; FIG. 8) utilize the concept of virtual electrodes, as described more fully above.

It will be recognized that the intrinsic line (160; FIG. 8) may not be completely linear across the entire frequency spectrum. Hence, in some embodiments, the intrinsic line (160; FIG. 8) may be represented by a number of concatenated lines each having a linear slope. The above described methods of adjusting the slope and/or position of the fitting line (161; FIG. 8) may therefore be applied to a number of segments of the fitting line (161; FIG. 8) such that the slope and/or position of each segment equals the slope and/or position of corresponding concatenated intrinsic lines (160; FIG. 8).

Figure 12:
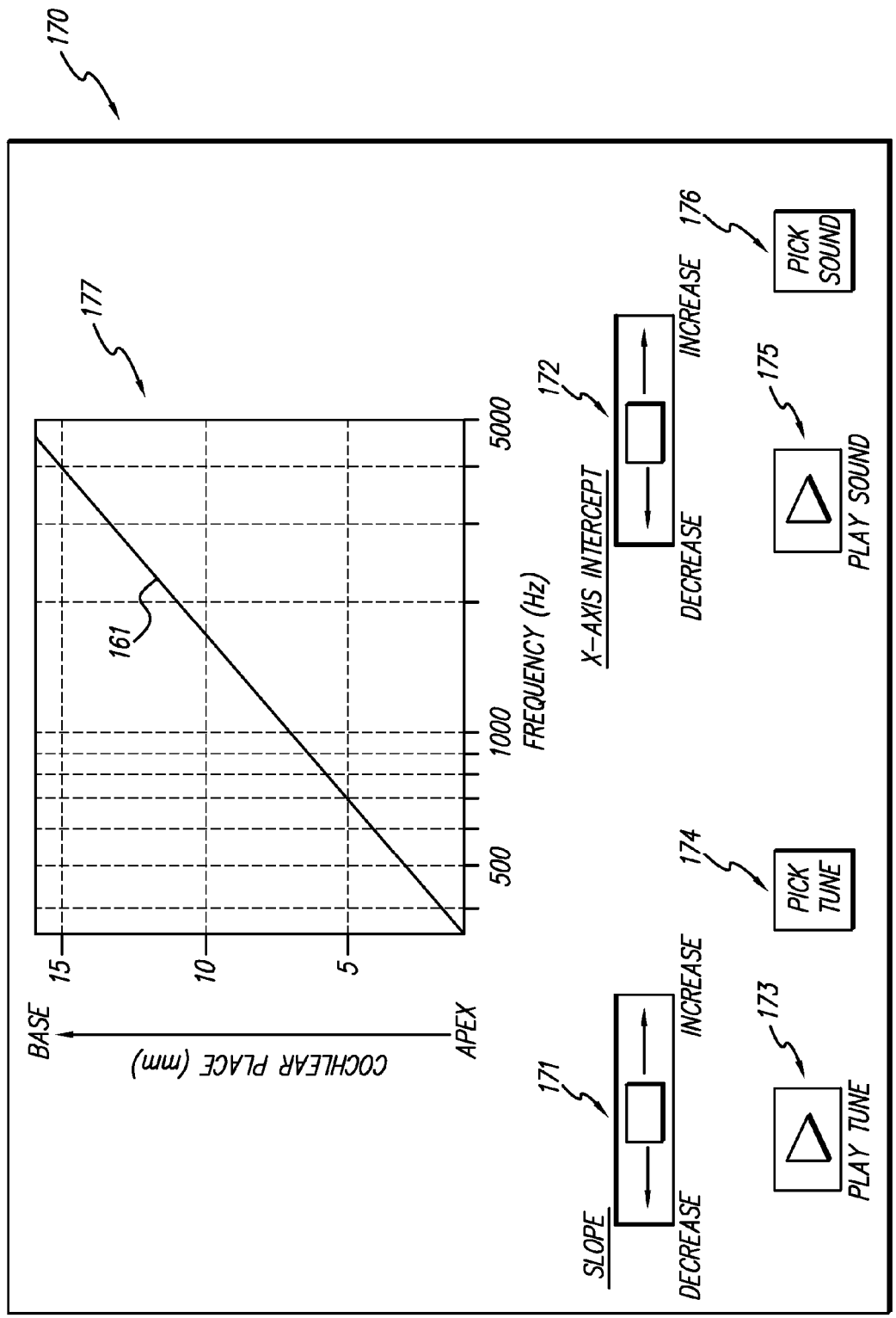
FIG. 12 illustrates an exemplary graphical user interface that may be used to adjust the slope and/or the position of the fitting line according to principles described herein.

The slope and/or the position of the fitting line (161; FIG. 8) may be adjusted by the cochlear implant patient, by a clinician, or by any other person using a variety of different control interfaces. For example, FIG. 12 illustrates an exemplary graphical user interface (GUI) (170) that may be used to adjust the slope and/or the position of the fitting line (161). The GUI (170) may include a graphical depiction (177) of the fitting line (161). The graphical depiction (177) may be configured to update automatically to reflect any change made by the patient or clinician in slope and/or position of the fitting line (161). A first sliding bar (171) may be included to allow the user of the GUI (170) to adjust the slope of the fitting line (161). A second sliding bar (172) may also be included to allow the user to adjust the X-axis intercept or position of the fitting line (161). The GUI (170) may also include buttons (173, 175), the selection of which plays a musical tune or a sound used in determining whether the slope and position of the fitting line (160) are correct. The GUI (170) may further include buttons (174, 176) configured to allow the user to select a musical tune from a list of available tunes and/or a sound from a list of available sounds.

The GUI (170) may be presented, in part, on a display monitor, for example, and may interface between the user and the cochlear implant system (20; FIG. 2). The commands input into the GUI (170) may be transmitted to a processor (not shown) or to any other component within the cochlear implant system (20; FIG. 2) such that the mapping scheme may be changed to reflect the change in slope and/or frequency of the fitting line (161).

It will be recognized that the GUI (170) presented in FIG. 12 is merely exemplary of the many different types and layouts of GUIs that may be used to facilitate the adjustment of the slope and/or position of the fitting line (161). Other control interfaces that may be used to adjust the slope and/or the position of the fitting line (161; FIG. 8) include, but are not limited to, a remote control and an analog tuning mechanism coupled to the cochlear implant system (20; FIG. 2).

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the claims.

What is claimed is:

1. A method for mapping cochlear locations to audio frequencies, the method comprising:
    applying a first signal and a second signal to locations within a user's cochlea through a multi-electrode array implanted into the user's cochlea, wherein particular frequencies are associated with particular electrodes;
    shifting the location where the first signal is applied to cause the user to perceive tonal variations of the first signal;
    allowing the user to select one of the tonal variations;
    shifting the pitch of both the second signal and the selected tonal variation of the first signal;
    allowing the user to select one of the pitch-shifted versions of both the second signal and the selected tonal variation of the first signal; and
    modifying the frequencies associated with the electrodes using the selected pitch-shifted version.

2. The method of claim 1, wherein the first signal has a known harmonic spacing from the second signal.

3. The method of claim 2, wherein the selected tonal variation of the first signal is perceived by the user as conforming to the known harmonic spacing.

4. The method of claim 2, wherein the selected pitch-shifted versions of both the second signal and the selected tonal variation of the first signal are perceived by the user as conforming to the known harmonic spacing.

5. The method of claim 1, wherein shifting the pitch comprises shifting the frequency of both the second signal and the selected tonal variation of the first signal so as to maintain the harmonic spacing between them.

6. The method of claim 1, wherein the first and second signals comprise notes in a musical tune.

7. The method of claim 1, wherein the first and second signals comprise frequencies in a sample of human speech.

8. A method for mapping cochlear locations to audio frequencies, the method comprising:
    (a) applying a first signal and a second signal to locations within a user's cochlea through a multi-electrode array implanted into the user's cochlea, wherein particular frequencies are associated with particular electrodes;
    (b) shifting the location where the first or second signals are applied to vary the tone between the first and second signals;
    (c) shifting the pitch of both the first and second signals;
    (d) allowing the user to select a shifted location and a shifted pitch from steps (b) and (c); and
    (e) modifying the frequencies associated with the electrodes using the selected shifted location and the selected shifted pitch.

9. The method of claim 8, wherein the first signal has a known harmonic spacing from the second signal.

10. The method of claim 9, wherein the selected shifted location corresponds to a tonal variation between the first and second signals that is perceived by the user as conforming to the known harmonic spacing.

11. The method of claim 9, wherein the selected shifted pitch corresponds to a pitch variation of both the first and second signals that is perceived by the user as conforming to a known musical tune.

12. The method of claim 9, wherein the selected shifted pitch corresponds to a pitch variation of both the first and second signals that is perceived by the user as conforming to a known sample of human speech.

13. The method of claim 8, wherein shifting the pitch comprises shifting the frequency of both the first and second signal.

14. The method of claim 8, wherein the first and second signals comprise notes in a musical tune.

15. The method of claim 8, wherein the first and second signals comprise frequencies in a sample of human speech.

* * * * *